United States Patent [19]

Lakshminarayanan

[11] 3,947,324

[45] Mar. 30, 1976

[54] METHOD FOR ISOLATING HIGH PURITY PEROXIDASE

[75] Inventor: Krishnaiyer Lakshminarayanan, Arlington Heights, Ill.

[73] Assignee: G. D. Searle and Co., Chicago, Ill.

[22] Filed: Apr. 21, 1975

[21] Appl. No.: 569,678

[52] U.S. Cl. ............................................... 195/66 R
[51] Int. Cl.$^2$ ........................................ C07G 7/022
[58] Field of Search ................................. 195/66 R

[56] References Cited
OTHER PUBLICATIONS

Methods in Enzymology, Vol. II, pp. 801–813 (1955).
Chemical Abstracts, Vol. 69, 74046v (1968).

*Primary Examiner*—Lionel M. Shapiro
*Attorney, Agent, or Firm*—John J. McDonnell

[57] ABSTRACT

The present invention encompasses a method for isolating peroxidase enzyme from plant tissue containing peroxidase. The invention has as its critical step treating an aqueous extract of said plant tissue having the pH adjusted to 6 – 9 with at least $2.7 \times 10^{-3}$ moles per liter of zinc ion. Unexpectedly at this pH the zinc ion selectively precipitates contaminating impurities from the extract and thereby provides a substantially purified peroxidase solution from which peroxidase is isolated by a variety of conventional techniques. Thus the critical step of the present invention is used in conjunction with salt fractionation, solvent fractionation, dialysis, reverse osmosis, electrophoresis, column chromatography and other techniques for purifying protein. The peroxidase isolated by methods of the present invention is useful in analytical diagnostic kits and other applications in enzyme and substrate assays in conjunction with a chromogenic donor in assaying systems producing hydrogen peroxide.

10 Claims, No Drawings

METHOD FOR ISOLATING HIGH PURITY PEROXIDASE

The present invention encompasses a method for isolating peroxidase enzyme from plant tissue containing peroxidase. This invention has as its critical step treating an aqueous extract of said plant tissue having the pH adjusted to 6 – 9 with at least $2.7 \times 10^{-3}$ moles per liter of zinc ion.

Peroxidase is an enzyme present in most plant tissue. It is present in figs and has an especially high concentration in horseradish (*Armoracia rusticana*) roots which is the preferred source of peroxidase. Aqueous extracts of diced or ground-up whole horseradish roots, horseradish skin extracts or washing, or washings of whole horseradish are suitable sources of peroxidase enzyme. The pH is adjusted to the 6 – 9 range with strong base such as sodium hydroxide. The preferred pH range is 7.5 to 8.5 and it is desirable to buffer the solution with a buffering agent such as disodium hydrogen phosphate. The aqueous extract is made at least $2.7 \times 10^{-3}$ molar in zinc ion by the addition of water soluble zinc salts such as zinc sulfate, zinc chloride, zinc acetate. The zinc ion concentration is preferably $2.7 \times 10^{-3}$ to $1 \times 10^{-1}$ moles per liter and $2.7 \times 10^{-2}$ to $1.4 \times 10^{-2}$ moles per liter is the most preferred zinc ion concentration. The aqueous phase may be saturated with zinc ion without adverse affects upon the critical feature of the present invention. The upper limits of zinc ion concentration are set primarly for economical use of inorganic zinc salts. The zinc ion forms a zinc ion-protein contaminant precipitate and this precipitate is removed from the extracts by filtration, centrifugation, or other techniques known to the art. The aqueous extracts are substantially purified by zinc treatment alone and the peroxidase enzyme is thereafter isolated and purified by conventional techniques known to those skilled in the art of protein separation. Thus the present invention is used in conjunction with other recognized isolation techniques such as salt fractionation, dialysis, solvent fractionation, electrophoresis, reverse osmosis, and column chromatography, to provide a more efficient method of producing peroxidase of high purity. The critical step representing the present invention may be used in conjunction with known methods for peroxidase isolation set out in *Proc. Roy Soc.* (London) B122, 119 (1937), Biochem. J. 49, 88 (1951), Enzymologia 1, 133 (1936), Enzymologia 10, 250 (1942), Biological Chemistry 241, 2166 (1966), and *Methods in Enzymology* II [143] pp 801, Academic Press, N.Y., N.Y. These methods generally include salt fractionation by ammonium sulfate, solvent fractionation by organic solvents such as methanol, ethanol, isopropanol, or acetone, dialysis, electrophoresis, and chromatography on media such as carboxymethyl cellulose. Once contaminants are precipitated by zinc ion at the concentration and pH set out above, those skilled in the protein separation arts will recognize a variety of methods for removing the precipitate and separating the peroxidase from the supernate. For example, the zinc ion-contaminant precipitate is removed by filtration or centrifugation and the peroxidase enzyme is isolated from the supernate by reverse osmosis followed by carboxymethyl cellulose column chromatography and solvent fractionation with isopropanol or ammonium sulfate salt fractionation followed by dialysis and isopropanol solvent fractionation. Thus the present invention is an improvement in a method for isolating peroxidase enzyme of the type including extraction, salt fractionation, dialysis, reverse osmosis, and solvent fractionation, the improvement which comprises treating aqueous extracts of said plant tissue having a pH adjusted to 6–9 with at least $2.7 \times 10^{-3}$ moles per liter of zinc ion to form a zinc ion-protein contaminant precipitate and supernate and removing the precipitate and separating the peroxidase from the supernate.

Preferably the pH is buffered at 7.5 – 8.5 and the zinc ion concentration is $2.7 \times 10^{-2}$ to $1.4 \times 10^{-2}$ moles per liter.

A preferred embodiment of the present invention is represented by a method for isolating peroxidase comprising:

a. extracting horseradish root with water;
b. adjusting the pH to 7.5 – 8.5;
c. adding $2.7 \times 10^{-3}$ to $1 \times 10^{-1}$ moles per liter of zinc ion to form a zinc ion — contaminant precipitate;
d. removing the precipitate by filtration or centrifugation;
e. removing zinc ion and low molecular weight organic material from the supernate by reverse osmosis to provide a concentrated supernate having a conductivity of 1–3 mMho;
f. absorbing the concentrated supernate on carboxymethyl cellulose at a pH of 4–7;
g. eluting peroxidase from the carboxymethyl cellulose with aqueous buffer having a pH of 7–9;
h. precipitating the peroxidase form the aqueous buffer with methanol, ethanol, dioxane, n-propanol, isopropanol, acetone or mixtures thereof, and
i. filtering and drying the precipitate.

A further preferred embodiment of the present invention is a process for the recovery of the enzyme peroxidase as a by-product of horseradish sauce manufacture from wash water. The process steps are equally applicable to horseradish roots. The root washings from horseradish operations are buffered with 2% $Na_2HPO_4$ to pH 8.0 and treated with 0.1 to 0.25%; w/v $ZnSO_4 \cdot H_2O$; foreign proteins are precipitated as insoluble Zn-complexes and the enzymic activity stabilized [stable at 5°C for 2 to 3 weeks]. The buffered Zn-complex of the enzyme is concentrated by reverse osmosis [R.O.]. [PM-10 Romicon membranes with 10,000 molecular weight cut off]. This step removes the water and all low-molecular weight impurities. The concentrated extract is again treated with zinc to deproteinize the supernate. The clear enzyme solution is concentrated by R.O. again. The enzymic activity is adsorbed on hydrated carboxymethyl cellulose [Sephedex C50] which absorbs about 70% of the total peroxidase activity available and the balance is recycled to the next batch; the carboxymethyl cellulose cake is washed and eluted with 2% NaAc at pH 8.7. Concentration, adsorption and elution steps are repeated to further purify the enzyme activity. The final eluate is precipitated with 2 volumes of isopropyl alcohol, filtered and dried in acetone to yield a product with RZ value >1; and peroxidase activity in the range 1000 to 3000 units per milligram.

The purity of peroxidase preparations is conventionally expressed in terms of RZ (Reinheitszhal) value. This number represents the ratio of optical density at 403 nm (due to the hemin group) to that at 275 nm (due to the protein). This ratio has been found to be 3.04 for pure crystalline horseradish peroxidase, Theorell and Maehly, Acta Chem. Scand. 4, 422 (1950).

A unit of peroxidase activity causes an increase of absorbance of 0.001 per minute at 460 nm using $H_2O_2$ as substrate and orthodianisidine as the hydrogen donor Worthington Enzyme Manuel, Worthington Biochem Corp., Freehold, N.Y. (1972) at pages 43–44.

The peroxidase product of the present invention is characterized as having an RZ value >1, an activity in the range of 1000 – 3000 units of peroxidase activity per milligram.

The present invention also encompasses a method for purifying substantially pure peroxidase having an RZ value of 0.1 to 1.5 comprising treating an aqueous solution of substantially pure peroxidase having a pH adjusted to 6 – 9 with at least $2.7 \times 10^{-3}$ moles per liter of zinc ion thereby forming a zinc ion-protein contaminant precipitate, and isolating the purified peroxidase, said peroxidase having an RZ value of 1.0 – 3.0. Typically substantially pure peroxidase having an RZ value 0.7 – 1.3 is purified to peroxidase having an RZ value of 2.3 – 3.0 without substantial loss of activity. It is evident that the zinc ion is selectively precipitating non-hemin containing proteins.

The selectivity of protein precipitation at the prescribed pH without loss of peroxidase activity represents the unexpected feature of the present invention. The prior art of fractionation and purification of proteins with heavy metal ions and zinc ion in particular is summarized in *Analytical Methods of Protein Chemistry* by Alexander and Block, Pergamon Press, 1960 at pages 20–22 and U.S. Pat. No. 3,284,316, Nov. 8, 1966. The former describes several proteins which are water soluble or insoluble in the presence of zinc ion and the latter describes a water soluble zinc papain complex.

The method of the present invention is particularly distinct in that zinc ion at a specified pH has been found to selectively precipitate contaminating proteins in aqueous peroxidase preparations.

Unlike the papain complex described in U.S. Pat. No. 3,284,316 which has 0.15 to 0.25% zinc complexed to the papain, the peroxidase enzyme prepared by the methods of the present invention contains only trace amounts of zinc ranging from about 200 – 400 parts per million. The peroxidase prepared by the methods of the present invention is stable for at least 3 weeks in aqueous solution without substantial loss of activity and the dry powder is stable for at least 3 months without any loss in activity.

The utility of peroxidase prepared by methods of the present invention is illustrated by its use as a reagent in the glucose oxidase method for determining glucose [*Clinical Laboratory Methods*, Bauer et al Mosby Co., St. Louis, 1974, Fales et ol Methods Clin. Chem. 4, 101, (1963), Kingsley, Clin. Chem. 6, 466 (1966)]. Glucose is oxidized by the enzyme glucose oxidase in the presence of air to gluconic acid with the formation of hydrogen peroxide. In the presence of the added enzyme, peroxidase, the hydrogen peroxide will oxidize the chromogen o-dianisidine to a compound that gives a red color in strongly acid solution. The reaction is very specific for glucose and thus gives true glucose values. High concentrations of reducing substances, particulary ascorbic acid, will interfere by competing with the chromogen for the liberated oxygen and thus cause low results. Hemoglobin will also interfer by causing premature decomposition of the hydrogen peroxide and also give low results. If hemoglobin is absent, the reaction can be run directly on serum or plasma.

REAGENTS

1. Phosphate buffer, 0.1M, pH 7.0. Dissolve 8.7 gm $Na_2HPO_4$ and 5.3 gm $KH_2PO_4$ in about 950 ml water. Check the pH and adjust to 7.0 if necessary with small amounts of 1N acid or base; then dilute to 1 L.

2. Buffered peroxidase solution. Mix 125 ml phosphate buffer, 175 ml water, and 200 ml glycerin. Dissolve 10 mg peroxidase in this solution, then add 100 mg o-dianisidine dissolved in 10 ml methanol, and mix well. Because of the added glycerin, this solution may be stored in the freezer compartment for added stability.

3. Glucose oxidase solution. Dissolve 500 mg glucose oxidase in 50 ml 40% glycerin. This may also be stored in the freezer.

4. Sulfuric acid, 30%. Carefully add 300 ml concentrated sulfuric acid to 700 ml water. Mix well and cool to room temperature.

PROCEDURE

Pipet 4.5 ml buffered peroxidase to a test tube. Warm to 37°C and add 0.02 ml serum or plasma. Add 0.5 ml glucose oxidase solution and incubate at 37°C for 30 min. After incubation, add 3 ml 30% sulfuric acid and mix. Run standards and blank similarly. Read standards and samples against blank at 530 nm.

CALCULATION

Since the standards and samples are treated similarly:

$$\frac{\text{Absorbance of sample}}{\text{Absorbance of standard}} \times \text{Conc. of standard} = \text{Conc. of sample}$$

The following examples are set out to illustrate the present invention and are not intended to limit the invention in spirit or scope.

EXAMPLE 1

Step I: Wash water from several batches of horseradish root washes from a rotary drum washer is collected at room temperature. The individual drum contents (with dirt) are treated with 1.0% (w/v) $Na_2HPO_4 2H_2O$ and the pH is adjusted to 8.0 with 25.0% NaOH. To this solution is added 0.1% $ZnSO_4H_2O$ as a 50% solution with mixing ($5.4 \times 10^{-3}$ molar is zinc ion). The mixture is allowed to settle for 15 hours at room temperature. The supernate is decanted and mixed with diatomaceous earth (celatom FW40) 2.0% w/v and filtered and recycled on 12" plate and frame filter, with the same filteraid. The clear filtrate is collected in stainless steel tanks, total volume is 8491.5 liters. This filtrate has 25.5 $\mu$/ml = $216.5 \times 10^6$ units of total peroxidase activity in the washes.

Step II: The clear filtrate is concentrated on hollow fiber membranes in a reverse osmosis unit (using PM10 membranes, made by Romicon) at approximately 18°C in batches and then the batches are pooled together. The combined concentrates are 91.4 liters having peroxidase activity of 2151 $\mu$/ml for a total peroxidase activity of $196.6 \times 10^6$ units.

Step III: The concentrate is treated with 0.5% w/v of $ZnSO_4H_2O$ as a 50% solution ($2.7 \times 10^{-2}$ molar in zinc ion) and the pH is adjusted to 8.0. The concentrate is mixed for 30 minutes and centrifuged on a Sharples centrifuge. This procedure gives a total centrifugate including washes of 100 liters having peroxidase activity of 1854 μ/ml. The heavy precipitate of zinc-protein complex is discarded.

Step IV: The supernatant from step III at pH 8.9 and conductivity of 10.5 mMho is reconcentrated with simutaneous dilution with deionized water on a reverse osmosis unit; the flow rates are adjusted to be approximately equal; the permeate with a negligable activity is discarded. This step gives a final volume of 35 liters having peroxidase activity of 4204 μ/ml which is a total peroxidase activity of 147.1 × 10⁶ units. The pH is 6.7 and conductivity is 1.3 mMho.

Step V: The concenrate from step IV is diluted to 160 liters with deionized water and the pH is adjusted to 5.0. The conductivity is 0.9 mMho. The diluted concentrate is treated with 34.5 kilos of wet Sephadex C50 (carboxymethyl cellulose, Pharmacia Fine Chemicals) mixed for 30 to 60 minutes and then filtered on Buchner on filter paper. The supernate has an activity of (170 liters × 300 μ/ml) or 51.0 × 10⁶ units. 34.7% of the total activity is not adsorbed. This latter portion is retained for salvage in a subsequent batch. Percentage adsorption on the carboxymethyl cellulose cake is 65.3% or 96.1 × 10⁶ units in the cake. The cake is washed with deionized water until washings are clear and then eluted in aliquots with 2.0% Sodium Acetate (NaAc 3H₂O w/v, pH 8.7) solution. The washings are combined to give 70 liters of eluated having peroxidase activity of 1548 μ/ml or 108.4 × 10⁶ total units of peroxidase activity.

Step VI: The combined eluates from step V are concentrated on a reverse osmosis unit to give a final volume of 17.8 liters having peroxidase activity of 5423 μ/ml or 96.5 × 10⁶ units of peroxidase activity total.

Step VII: The concentrate from step VI is treated with 0.25% ZnSO₄H₂O w/v (1.35 × 10⁻² molar in zinc ion), the pH is adjusted to 8.0, centrifuged and the resulting sediment is discarded. The centrifugate is 17.5 liters having peroxidase activity of 4811 μ/ml or 84.2 × 10⁶ units total peroxidase activity.

Step VIII: Isopropanol (technical, purity 99%) is chilled to −10°C (in dry ice acetone bath) and 35 liters of the chilled solvent is added to 17.5 liters of the peroxidase concentrate from step VII (pH 7.5). This combination is mixed for 30 minutes, centrifuged and the solvent is discarded. The precipitate from the centrifuge bowl is treated with the chilled acetone 99% at −10°C, blended, filtered on a Buchner, washed with acetone, and dried at room temperature to give a final product of 26.8 grams having peroxidase activity of 1436 μ/ml with an RZ value of 1.1. Total peroxidase activity is 38.5 × 10⁶ units.

EXAMPLE 2

Step I: Horseradish root washings from the rotary drum washer are collected in several 55 gallon drums and treated with 1.0% w/v Na₂HPO₂ 2H₂O. The pH is adjusted to 8.0, ZnSO₄H₂O is added as a 50% solution to give a concentration of 0.1% w/v (5.4 × 10⁻³ molar in zinc ion) and this mixture is allowed to settle at room temperature, the supernatant is mixed with 2.0% FW40 diatomaceous earth and filtered. The combined filtrate is 540 liters having peroxidase activity of 49 μ/ml. The total peroxidase activity is 26.5 × 10⁶ units.

Step II: The filtrate from step I is concentrated on a reverse osmosis unit using PM10 membranes at 18°C. The permeate having negligible activity is discarded. The concentrate is 12.7 liters having peroxidase activity of 2076 μ/ml for a total peroxidase activity of 26.4 × 10⁶ units.

Step III: The concentrate from step II is treated with 0.5% w/v ZnSO₄H₂O (2.7 × 10⁻² molar in zinc ion). The pH is adjusted to 8.0 and mixture is centrifuged. The sediment is discarded and the centrifigate including the washes have a volume of 18.8 liters and an activity of 1215 μ/ml for a total peroxidase activity of 22.8 × 10⁶ units.

Step IV: The centrifigate from step III has a conductivity of 8.8 mMho and pH 8.0. This centrifugate is desalted, diluted with deionized water and concentrated simultaneousy on a reverse osmosis unit. The permeate is discarded and the concentrate has a conductivity of 1.8 mMho (pH 7.5), volume 9.8 liters having peroxidase activity of 2565 μ/ml for a total peroxidase activity of 25.1 × 10⁶ units.

Step V: The concentrate from step IV is diluted to 29.4 liters with deionized water and the pH is adjusted to 5.0. This solution has a conductivity of 0.55 mMho and assays at 787 μ/ml. 5.88 kilos of wet Sephadex C50 is added and mixed for 30 minutes and then filtered on a Buchner. The filtrate and washings are combined to give 32.7 liters activity 395 μ/ml for a total activity of 12.9 × 10⁶ units. This material is retained for salvage with subsequent batches. The sephadex cake has 10.2 × 10⁶ units of the peroxidase activity; the cake is eluted with aliquots of 2.0% NaAc (w/v) pH 8.7 solution to give a combined eluate of 11 liters having peroxidase activity of 1085 μ/ml for a total peroxidase activity of 11.9 × 10⁶ units.

Step IV: The combined eluate from step V is concentrated as previously described by reverse osmosis to give 2.65 liters of concentrate having peroxidase activity of 3820 μ/ml for a total peroxidase activity of 10.1 × 10⁶ units.

Step VII: The concentrate from step VI is treated with 0.25% ZnSO₄H₂O (1.35 × 10⁻² molar in zinc ions) at pH 8.0 and centrifuged. The precipitate of zinc protein complex is discarded. The centrifugate is 2.65 liters having peroxidase activity of 3508 μ/ml for a total peroxidase activity of 9.3 × 10⁶ units.

Step VIII: The concentrated peroxidase from step VII (2.65 liters) is treated with 5.3 liters of Isopropanol (technical 99% pure) at −10°C for 30 minutes and centrifuged. The precipitate is washed in acetone and dried to give 3.110 grams of peroxidase having an activity of 1626 μ/ml for a total peroxidase activity of 5.1 × 10⁶ units having an RZ value of 2.1.

EXAMPLE 3

A sample of horseradish peroxidase was collected from the rotary drum washer and aliquots of the sample treated with ZnSO₄H₂O; NaCl; Na₂HPO₄2H₂O, mixed for 15 minutes, centrifuged and the centrifugate assayed for peroxidase activity. Results are presented in Table I.

Table 1

| Treatment | Peroxidase in μ/ml |
|---|---|
| 1. As is untreated | 47 |
| 2. Centrifuged | 35 |
| 3. 0.1% ZnSO₄H₂O added and centrifuged | 31 |
| 4. 0.1% ZnSO₄H₂O plus 2.0% Na₂HPO₄ 2H₂O added, centrifuged | 50 |
| 5. 0.1% ZnSO₄H₂O plus 5.0% Na₂HPO₄ 2H₂O added, centrifuged | |

Table 1-continued

| | Treatment | Peroxidase in $\mu$/ml |
|---|---|---|
| | and assayed | 55 |
| 6. | 0.1% ZnSO$_4$H$_2$O plus 2.0% Na$_2$HPO$_4$ 2H$_2$O plus 3.0% NaCl | 54 |
| 7. | 0.1% ZnSO$_4$ plus 2.0% Na$_2$HPO$_4$ 2H$_2$O plus 5.0% NaCl | 58 |

EXAMPLE 4

A commercial preparation of peroxidase (of RZ value 1.0) is dissolved in deionized water to give a solution assaying 2262 $\mu$/ml.

To 200 ml of this solution is added 40 grams of wet Sephadex C50 (washed and equalibrated to pH 5.0). The pH is adjusted to 5.0, mixed for 30 minutes, and filtered. The filtrate is assayed — 69 $\mu$/ml showing a % adsorption of 97%.

The cake is washed in deionized water and eluted with 3 aliquots of 2.0% sodium acetate solution, having a pH 8.7. The combined eluate (115 ml) has peroxidase activity of 2707 $\mu$/ml and has an RZ value of 1.3.

A 50 ml aliquot of this eluate is treated with 125 mgs of ZnSO$_4$H$_2$O (1.35 × 10$^{-2}$ molar per liter in zinc ion) and centrifuged. The centrifugate has peroxidase activity of 2493 $\mu$/ml having an RZ value of 2.4.

Another 50 ml aliquot of the original eluate is treated with 0.25 grams of ZnSO$_4$H$_2$O (2.7 × 10$^{-2}$ molar per liter in zinc ion). The pH is adjusted to 8.0 and centrifuged. The centrifugate has peroxidase activity of 2412 $\mu$/ml and has an RZ value of 2.5 as compared with an RZ value of 1.3 on the eluate and 1.0 on the original enzyme.

EXAMPLE 5

A commercial sample of peroxidase in dissolved in 2.0% NaAc3H$_2$O solution having a pH 8.0 to give a solution assaying at 2277 $\mu$/ml of peroxidase activity with an RZ value of 1.1.

50 ml of this solution is treated with 125 mg of ZnSO$_4$H$_2$O (zinc ion ioncentration of 1.35 × 10$^{-2}$ moles per liter) at pH 8.0 mix for 15 minutes and centrifuged. The centrifugate has 1935 $\mu$/ml of peroxidase activity having an RZ value of 1.6.

Another 50 ml aliquot of the same solution is treated with 250 mg of ZnSO$_4$H$_2$O (0.5% w/v) at pH 8.0 mix for 15 minutes and centrifuged. The centrifugate has 1704 $\mu$/ml of peroxidase activity having an RZ value of 2.1.

EXAMPLE 6

A combined NaAc eluate of Sephadex cake containing peroxidase is adsorbed and eluted as per examples 1 and 2. The assay is 724 $\mu$/ml of peroxidase activity with an RZ value of 1.1. 50 ml of this solution is treated with 250 mg of ZnSO$_4$H$_2$O and the pH is adjusted to 8.0. The solution is mixed for 15 minutes and centrifuged; the centrifugate has peroxidase activity of 717 $\mu$/ml and an RZ value of 2.6.

EXAMPLE 7

200 mg of a commercial peroxidase preparation assaying at 1300 $\mu$/mg of peroxidase activity is dissolved in 14 ml of 0.05 M phosphate buffer pH 7.0. To this buffered solution is added 28 ml of ice cold isopropanol (−10°C). The solution is mixed for 10 minutes and centrifuged. The sediment is washed with an aliquot of isopropanol again, suspended in acetone, filtered on a Buchner, and dried. This procedure provides 166.1 mg of peroxidase enzyme having 1533 $\mu$/mg of peroxidase activity for a recovery of 98% in the precipitate.

EXAMPLE 8

200 mg of a commercial peroxidase preparation assaying at 1300 $\mu$/mg is dissolved in 14 ml of 2.0% NaAc 3H$_2$O solution (pH 8.0) and 28 ml of ice cold isopropanol at −10°C is added. The solution is mixed for 15 minutes and centrifuged. The sediment is washed with isopropanol, filtered on Buchner, and dried in acetone to provide 139 mg a peroxidase enzyme assaying at 1785 $\mu$/mg giving a recovery of 95%.

What is claimed is:

1. A method for isolating peroxidase enzyme from plant tissue containing peroxidase enzyme comprising treating aqueous extracts of said plant tissue having a pH adjusted to 6 – 9 with at least 2.7 × 10$^{-3}$ moles per liter of zinc ion to form a zinc ion-protein contaminant precipitate and supernate, removing the precipitate, and separating the peroxidase enzyme from the supernate.

2. The method according to claim 1 for isolating peroxidase enzyme from horseradish root comprising treating aqueous extracts of horseradish roots having a pH adjusted 6 – 9 with at least 2.7 × 10$^{-3}$ moles per liter of zinc to form a zinc ion-protein contaminant precipitate and supernate, removing the precipitate, and separating the peroxidase enzyme from the supernate.

3. The method according to claim 1 wherein the pH is 7.5 – 8.5 and the zinc ion concentration is 2.7 × 10$^{-2}$ to 1.4 × 10$^{-2}$ moles per liter.

4. In a method for isolating peroxidase enzyme from plant tissue containing peroxidase enzyme of type including extraction, salt fractionation, dialysis, and solvent fractionation, the improvement which comprises treating aqueous extracts of said plant tissue having a pH adjusted to 6 – 9 with at least 2.7 × 10$^{-3}$ moles per liter of zinc ion to form a zinc ion protein contaminant precipitate, removing the precipitate and separating the peroxidase enzyme from the supernate.

5. A method for further purifying substantially pure peroxidase having protein contaminant and having an RZ value of 0.1 to 1.3 comprising treating an aqueous solution of substantially pure peroxidase having a pH adjusted to 6 – 9 with at least 2.7 × 10$^{-3}$ moles per liter of zinc ion thereby forming a zinc ion protein contaminant precipitate, separating the precipitate, and isolating the purified peroxidase having an RZ value from 1.0 – 3.0.

6. A method as in claim 1 wherein the source of peroxidase is horseradish root washings.

7. A method as in claim 1 wherein the zinc ion concentration is 2.7 × 10$^{-3}$ to 1 × 10$^{-1}$ moles per liter.

8. A method as in claim 1 wherein the peroxidase is separated from the supernate by reverse osmosis.

9. A method as in claim 8 wherein the peroxidase is further separated from the supernate by absorption on carboxymethyl cellulose.

10. A method according to claim 1 for isolating peroxidase comprising:
 a. extracting horseradish root with water,
 b. adjusting the pH to 7.5 – 8.5,
 c. adding 2.7 × 10$^{-3}$ to 1 × 10$^{-1}$ moles per liter of zinc ion to form a zinc ion — contaminant precipitate,
 d. removing the precipitate by filtration or centrifugation, e. removing zinc ion and low molecular weight organic material from the supernate by reverse osmosis to provide a concentrated supernate having a conductivity of 1 – 3 mMho, f. absorbing the concentrated supernate on carboxymethyl cellulose at a pH of 4 – 7, g. eluting peroxidase from the carboxymethyl cellulose with aqueous buffer having a pH of 7 – 9, h. precipitating the peroxidase form the aqueous buffer with methanol, ethanol, dioxane, propanol, isopropanol, acetone or mixtures thereof, and i. filtering and drying the precipitate.

* * * * *